(12) United States Patent
Bunce et al.

(10) Patent No.: US 6,309,117 B1
(45) Date of Patent: Oct. 30, 2001

(54) SYSTEM AND METHOD FOR ADJUSTMENT OF COLOR PRESENTATION IN NETWORKED MEDIA

(75) Inventors: Thomas M. Bunce, Allen; Dan Watson, Dallas, both of TX (US)

(73) Assignee: Nortel Networks Limited, Quebec (CA)

(*) Notice: Subject to any disclaimer, the term of this patent is extended or adjusted under 35 U.S.C. 154(b) by 0 days.

(21) Appl. No.: 09/640,009

(22) Filed: Aug. 17, 2000

(51) Int. Cl.[7] .................................. B41J 5/30; A61B 3/02
(52) U.S. Cl. .............................................. 400/61; 351/237
(58) Field of Search ........................ 400/61; 351/237, 351/239

(56) References Cited

U.S. PATENT DOCUMENTS

| 5,568,209 | * | 10/1996 | Priester et al. ................ 351/243 |
| 5,589,898 | * | 12/1996 | Atkinson ........................ 351/237 |
| 5,694,199 | * | 12/1997 | Rodriguez ...................... 351/223 |
| 5,943,116 | * | 8/1999 | Zeimer .......................... 351/221 |
| 5,946,075 | * | 8/1999 | Horn ............................ 351/246 |
| 6,045,515 | * | 4/2000 | Lawton .......................... 600/558 |

* cited by examiner

Primary Examiner—John S. Hilten
Assistant Examiner—Charles H. Nolan, Jr.
(74) Attorney, Agent, or Firm—Hunton & Williams

(57) ABSTRACT

A system for adjusting the RGB or other color scheme of a Web page or other network media first tests a user for color compromise in their vision, for instance to determine if a user has a green or red color deficiency or other compromise. The system generates a translation between a Web page's existing color scheme and an adjusted scheme which is tailored to that individual's vision characteristics. The color translation profile may be stored as a cookie, digital certificate or other data object for retrieval and use on an existing or newly visited Web page, or may be dynamically adjusted with each new use.

31 Claims, 4 Drawing Sheets

(2 of 4 Drawing Sheet(s) Filed in Color)

SYSTEM AND METHOD FOR ADJUSTMENT OF COLOR PRESENTATION IN NETWORKED MEDIA

FIELD OF THE INVENTION

The invention relates to the field of networked media, and more particularly to a technique for replacing the color schemes on Web pages or other media with different color schemes which are viewable by persons with color-impaired vision.

BACKGROUND OF THE INVENTION

Web pages and other networked media are often presented in complex color schemes, to enhance the design, functionality or advertising attractiveness of a Web property or other site. For instance, commercial advertising such as banners or Java-coded animations are often presented in brighter or more eye-catching color. Important regions of a Web page, for instance input boxes or specific output fields such as account balance or other financial data lines, may likewise be highlighted using a brighter color, border or backdrop for that area.

However, not every individual viewing a Web page or other media is capable of discerning the color accents on a Web page or other site. Due to pigment sensitivity in the cone clusters of the macula or other physiological and genetic factors of the eye, some people may not be able to see certain ranges of visible light, which is generally in the range of 400 to 700 nm.

Thus, some people may not be able to discern green wavelengths (which is referred to as deutanomalous, or green weak condition) or red wavelengths (protanomalous, red weak condition) very well, or more rarely may be incapable of discerning color at all (monochromasy). These conditions alter the perceived Web content for such persons. A Web site which for example indicates bank account, mutual fund or other data in color coded bar graphs may thus appear pale, indistinct or color-shifted to a person having deficits in the color ranges used to encode those graphs. Reading the page and inputting information into that page may be difficult to that person.

Approximately 0.5% of the female population and 5-8% of the male population are estimated to have color compromised vision of one type or another. Web pages or other media sites that do not take a certain variability in the vision of viewers into account thus may lose the ability to reach a portion of the potential audience. While some standard color tests are known in the optical arts, those tests are manual and generally not designed to be integrated with Web or other networked media. For instance, the charts shown in FIG. 1 reflect the Ishihara test whose hues are selected to detect color deficiencies, including red weak and green weak. Other tests are known.

However, simply knowing the results of an Ishihara or other color sensitivity test does not by itself enable a Web user to correct the color displays for the media they wish to access. More universal and flexible technology for adjusting the color schemes of Web and other media is desirable.

SUMMARY OF THE INVENTION

The invention overcoming these and other problems in the art relates to a system and method for the adjustment of color presentation in Web or other networked media, in which an interrogator module may query a user to determine perceived hues and generate a color perception profile for that user. The color perception profile may be used to adjust Web pages and other media according to that user's color sensitivity, for instance by mapping the existing color scheme on the Web page or other media to a new color-scheme within the range of that user's vision.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The invention will be described with reference to the accompanying drawings, in which like elements are referenced with like numerals.

DETAILED DESCRIPTION OF PREFERRED EMBODIMENTS

Figure 1:
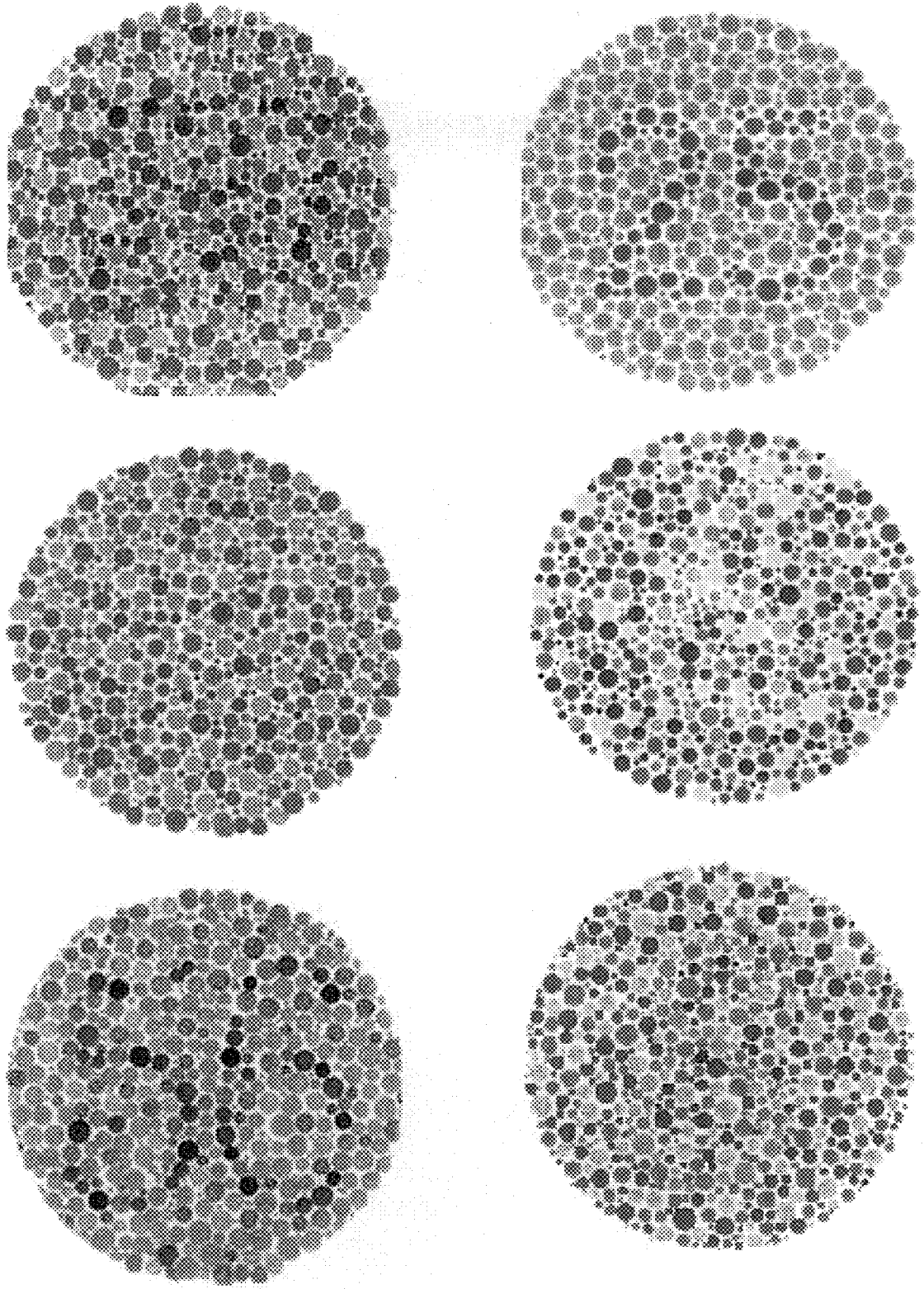
FIG. 1 illustrates a known Ishihara test for detecting color sensitivity.
Figure 2:
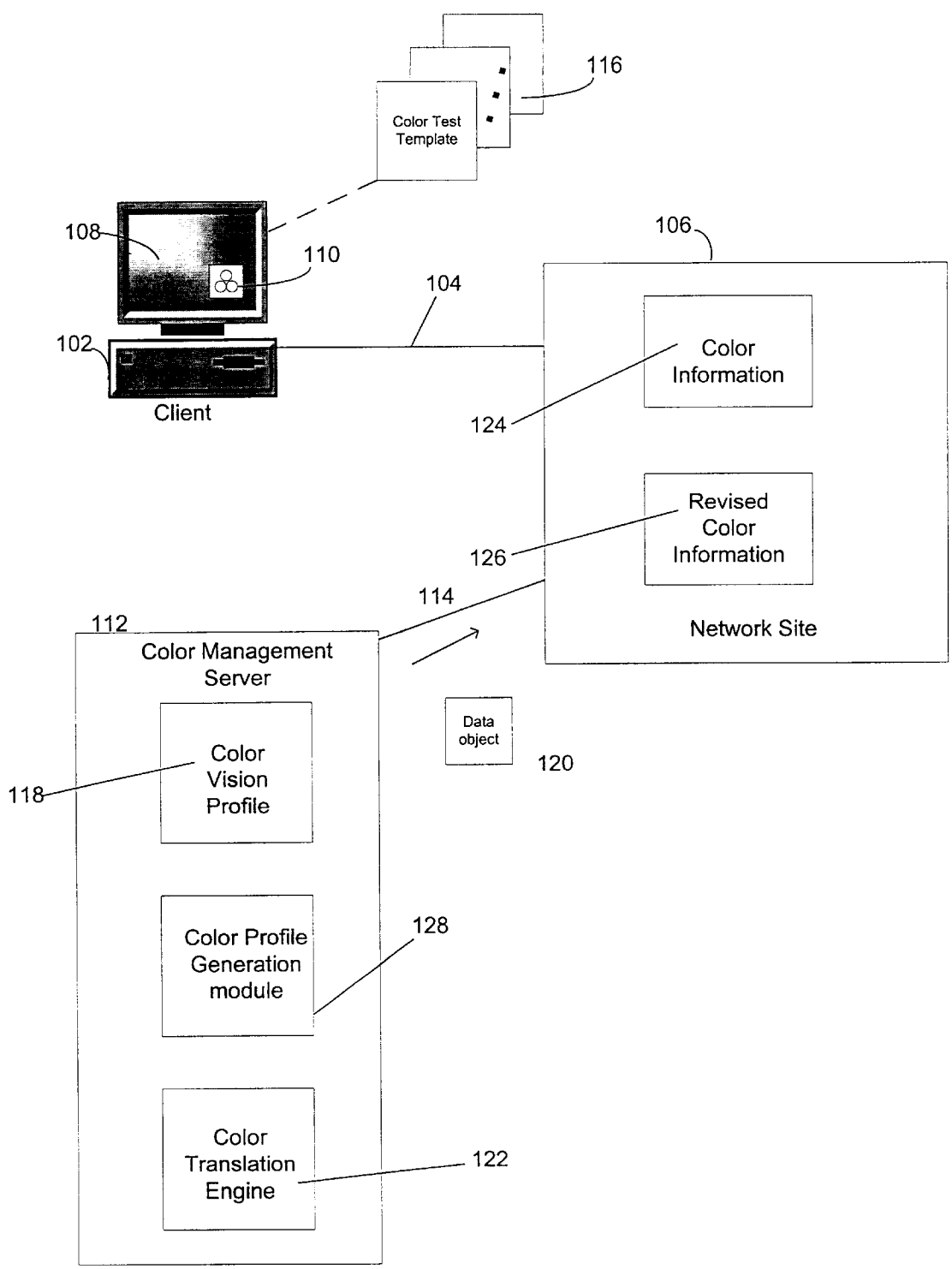
FIG. 2 illustrates a color adjustment system according to an embodiment of the invention.

As illustrated in FIG. 2, in an embodiment of the invention a client 102 can access a network site 106, such as a Web site, via communications link 104. A user can use the network site 106 for instance to view news or other information, log into a financial or other account, conduct a purchase transaction or other activities. The client 102 (or clients) through which the user views the network site 106 can include, for instance, a personal computer running Microsoft Windows™ 95, 98, Millenium™, NT™, or 2000, Windows™CE™, PalmOS™, Unix, Linux, Solaris™, OS/2™, BeOS™, MacOS ™ or other operating system or platform. Client 102 may also be or include a network-enabled appliance such as a WebTV™ unit, radio-enabled Palm™ Pilot or similar unit, a set-top box, a networkable game-playing console such as Sony Playstation™ or Sega Dreamcast™, a browser-equipped cellular telephone, or other TCP/IP client or other device.

The communications link 104 over which the client 102 access the network site 106 may include or interface to any one or more networks such as, for instance, the Internet, an intranet, a PAN (Personal Area Network), a LAN (Local Area Network), a WAN (Wide Area Network) a MAN (Metropolitan Area Network), or a storage area network (SAN). Network site 106 may also include or interface with various types of connections such as, for example, a frame relay, an Advanced Intelligent Network (AIN), a synchronous optical network (SONET), a digital T1, T3, E1 or E3 lines, Digital Data Service (DDS), DSL (Digital Subscriber Line), Ethernet, ISDN (Integrated Services Digital Network), dial-up ports such as V.90, V.34 or V.34bis analog modems, cable modems, ATM (Asynchronous Transfer Mode), or an FDDI (Fiber Distributed Data Interface) or CDDI (Copper Distributed Data Interface).

Communications link 104 can further, include or interface to any one or more of, for example, a WAP (Wireless Application Protocol) link, a GPRS (General Packet Radio Service) link, a GSM (Global System for Mobile Communication) link, a CDMA (Code Division Multiple Access) or TDMA (Time Division Multiple Access) link such as a cellular phone channel, a GPS (Global Positioning System) link, CDPD (cellular digital packet data), a RIM (Research in Motion, Limited) duplex paging type device, a Bluetooth radio link, or an IEEE 802.11-based radio frequency link. Communications link 104 may yet further be, include or interface to any one or more, for example, of an RS-232 serial connection, an IEEE-1394 (Firewire) connection, a Fibre Channel connection, an IrDA (infrared) port, a SCSI (Small Computer Systems Interface) connection, a USB (Universal Serial Bus) connection or other wired or wireless, digital or analog interface or connection. Other communications links illustrated herein may be, include or interface to similar communications resources. The above examples of communications and other resources are illustrative rather than exhaustive, as will be apparent to these skilled in the art.

The client 102 can display to the user a user interface 108 through which graphical, textual, video, audio or other media are presented to the user to use and navigate the network site 106. In one embodiment, the user interface 108 can display a graphical desktop including file, mouse, printing and other icons known in the art, for instance on a CRT, LCD or other display screen.

Network site 106 can, in an embodiment shown in FIG. 2, present the user with a color management icon 110 which can be activated by mouse click, keyboard, touchscreen, pen pad, voice activation or other techniques. The network site 106 may be or include, for example, an account login page or a shopping site displaying books, records, video or other media for sale or rent in a variety of colors, icons and other graphical elements on user interface 108.

As illustrated in FIG. 2, activation of color management icon 110 can link the user to a color management server 112 via communications link 114 located at a site remote from network site 106. The activation of color management icon 110 can initiate a color profile generation module 128 which presents the user with a series of predetermined color test templates 116. The color test templates 116 can contain a series of patterns designed to detect green weak, red weak or other color deficits. In one embodiment, the color test templates 116 can include the Ishihara test protocol. However, other protocols may also be used without departing from the spirit and scope of the present invention.

The user who is operating client 102 can respond to the color test templates 116 by graphical mouse or other response via the user interface 108 to indicate the colors, characters, figures or patterns visible to them in the color test templates 116. These responses can be collected by the color profile generation module 128 to generate a color vision profile 118.

The color vision profile 118 can, for instance, record data fields indicating a percentage reduction in the viewer's sensitivity to green, red or other hues, along with other information such as luminance sensitivity, focal abilities, astigmatic tendencies or other vision-related information. The resulting color vision profile 118 generated after these interactive tests can be stored locally in color management server 112. Alternatively, the color vision profile 118 can also be generated and stored in a cookie, digital certificate or other data object 120 for transmission and storage on client 102, or elsewhere.

The user can then be presented with a dialog box or other input option to adjust the displayed network site 106 according to that person's color vision profile 118. If the user desires to alter the displayed color scheme of the network site 106, the color management server 112 can may invoke a color translation engine 122 to parse the existing color layout of the network site 106. That examination can determine color settings such as bit mapped color depth, dithering or compression settings, RGB or CMYK values, histogram, HTML or other color information 124.

The color translation engine 122 can then access the color vision profile 118 of the user, and apply mappings or transformations to the color information 124 to generate revised color information 126 appropriate for that user. For instance, if the user's color vision profile 118 indicates a red deficiency, hues toward the red (lower) range of the visible spectrum can be offset by a predetermined or variable amount. For example, the color translation engine 122 can adjust the color scheme by shifting red spectral hues by 100 nm of wavelength, or reducing 20% of the RGB red component, or reducing the red portion in the color histogram of the page to 10%. The revised color information 126 thus can eliminate or shift displayed images out of that color band. Other substitution algorithms can be used, for instance to transform the color information 124 to grayscale, including for persons having a condition of total color blindness.

Figure 3:
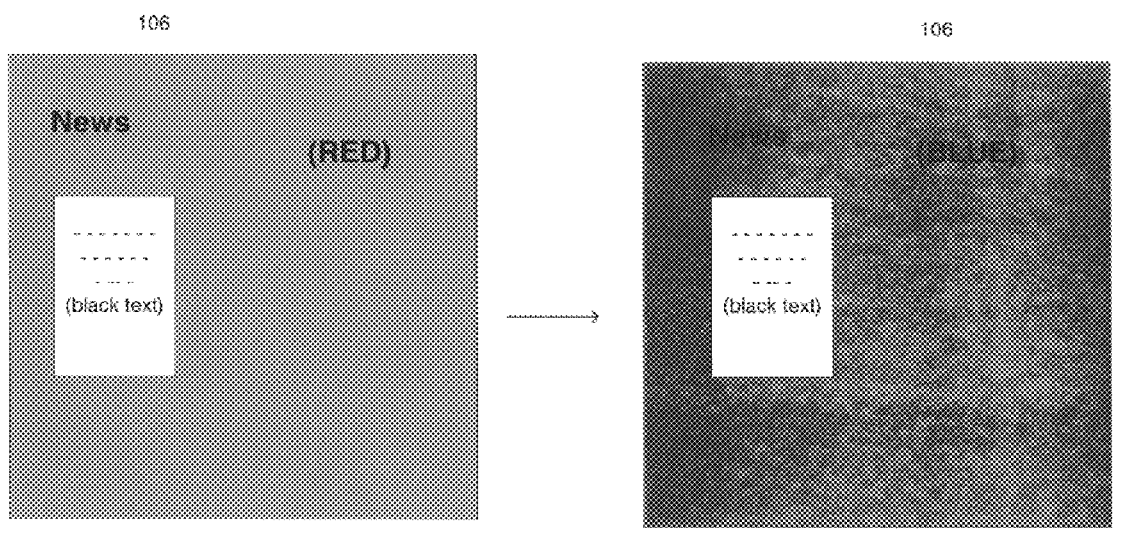
FIG. 3 illustrates Web or other media output generation according to an embodiment of the invention.

However, the color translation engine 122 can preferably attenuate, suppress or alter as many hues which the user has difficulty viewing as possible, so that the structure of screen icons, dialog boxes and other input/output, textual and other information on network site 106 can be preserved in the revised color information 126 but presented in a different spectral scheme, as illustrated in FIG. 3. Again, in one embodiment the color vision profile 118 can be communicated to the client 102 via data object 120 for automatic distribution to further network sites 106 having a connection to color management server 112 or compatible color management resources.

For instance, the data object 120 in one embodiment can include a cookie stored on a hard drive of client 102, or in another embodiment be transmitted to a Web browser such as Microsoft Internet Explorer™ for storage and use as a plug-in that the user can invoke or apply to any compatible Web sites. Alternatively, the user may wish to deactivate the data object 120 or other trigger for the color management system of the invention. The user can then activate new testing and an updated color vision profile 118 on a site-by-site, periodic or other basis.

Figure 4:
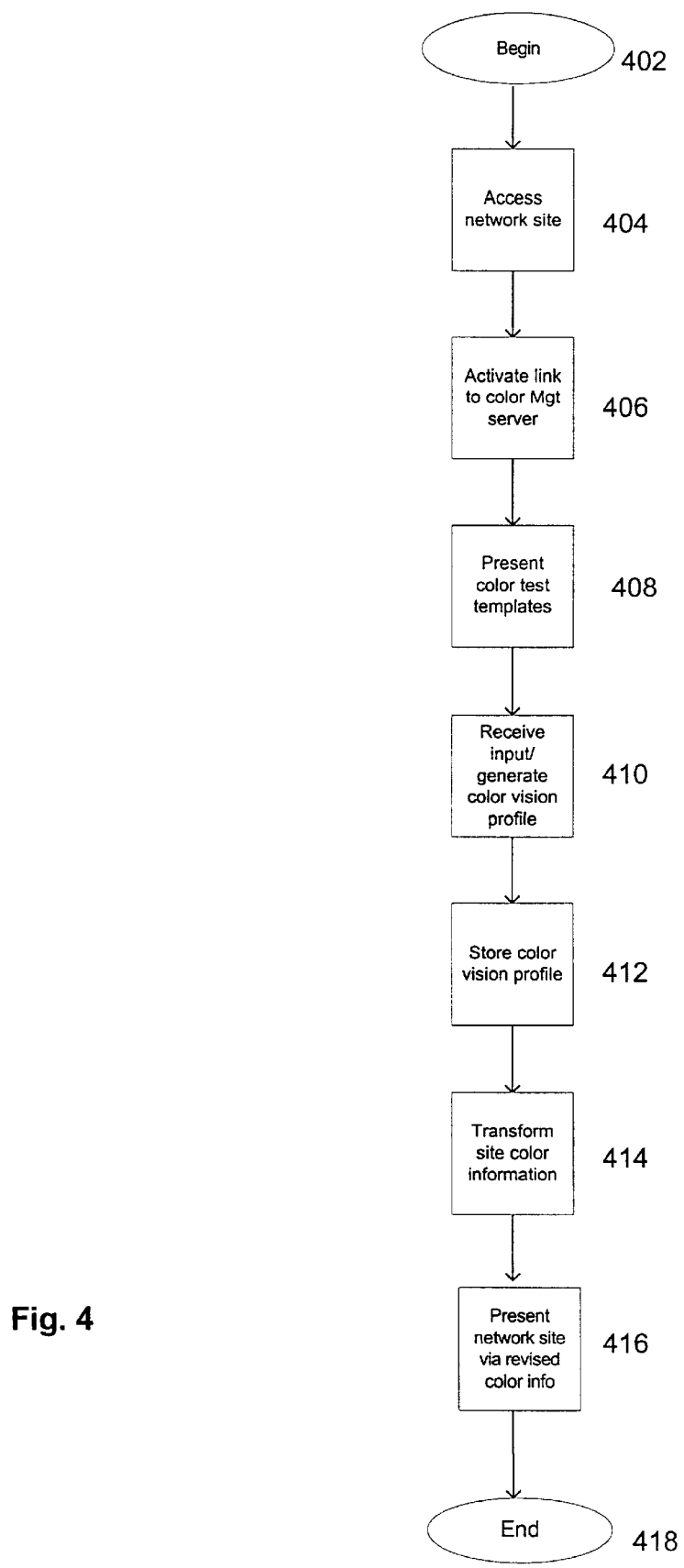
FIG. 4 illustrates a flowchart of color processing according to an embodiment of the invention.

A flowchart of color management processing is illustrated in FIG. 4. In step 402, processing begins. In step 404, a user can access a network site 406 via client 102. In step 406, the user can activate a link to the color management server 112, such as by a special screen icon. In step 408, the user can be presented with the color test templates 116, in a predetermined sequence and recording user responses to perceived colors, shapes, text and other information. In step 410, the color profile generation module 128 can receive the user's responses and generate a color vision profile 118 for that user. In step 412, the color vision profile 118 can be stored on color management server 112, on client 102 or elsewhere within the network or offline.

In step 414, the color information 124 pertaining to the network site 106 can be transformed by the color translation engine 122 to generate the revised color information 126. In step 416, the screen display or other output of network site 106 can be presented using revised color information 126. In step 418, processing ends.

The foregoing description of the system and method of the invention is illustrative, and variations in configuration and implementation will occur to persons skilled in the art. For instance, while the color management server 112 and associated resources have been described as being remote from network site 106, the functions of the color management server 112 may be partly or wholly integrated in network site 106. Other computing or other resources described as separate can be combined into one, or computing or other resources described as singular can be distributed amongst different platforms in different implementations.

The scope of the invention is accordingly intended to be limited only by the following claims.

What is claimed is:

1. A system for the adjustment of a color scheme in a networked media, comprising:
    a vision test module at a first location, the vision test module interrogating a user via a user interface to generate a vision characteristic profile for the user; and
    a color translation engine at a second location comprising a second storage for storing the vision characteristic profile, the color translation engine communicating with the vision test module and generating a mapping from a first color scheme in a first site at a third location in a networked media to a second color scheme according to the vision characteristic profile, where the first location, the second location and the third location are remote from one another.

2. The system of claim 1, wherein the vision test module comprises a plurality of color test templates.

3. The system of claim 1, wherein the vision characteristic profile comprises color sensitivity information.

4. The system of claim 3, wherein the color translation engine generates the mapping based at least on the color sensitivity information.

5. The system of claim 4, wherein the mapping comprises at least a reduction in deficient hues for the user indicated by the color sensitivity information.

6. The system of claim 1, wherein the vision test module interrogates the user upon activation of a screen element by the user.

7. The system of claim 1, wherein the vision characteristic profile is stored at least in a second storage in a client operated by the user.

8. The system of claim 1, wherein the color characteristic profile is stored in a transmissable data object.

9. The system of claim 8, wherein the transmissable data object is operable to automatically activate the mapping at a second network site in the networked media.

10. The system of claim 1, wherein the networked media comprises the Internet.

11. A method for the adjustment of a color scheme in a networked media, comprising:
    interrogating a user with a vision test via a user interface at a first location to generate a vision characteristic profile for the user, wherein the vision characteristic profile is stored at least in a storage at a second location; and
    generating a mapping from a first color scheme in a first site at a third location in a networked media to a second color scheme according to the vision characteristic profile, where the first location, the second location and the third location are remote from one another.

12. The method of claim 11, wherein the step (a) of interrogating the user with a vision test comprises a step of c) presenting a plurality of color test templates to the user.

13. The method of claim 11, wherein the vision characteristic profile comprises color sensitivity information.

14. The method of claim 13, wherein the color translation engine generates the mapping based at least on the color sensitivity information.

15. The method of claim 14, wherein the step (b) of generating a mapping comprises a step of d) at least reducing deficient hues for the user indicated by the color sensitivity information.

16. The method of claim 11, wherein the step a) of interrogating the user with a vision test comprises a step of e) interrogating the user upon activation of a screen element by the user.

17. The method of claim 11, wherein the vision characteristic profile is stored at least in a second storage in a client operated by the user.

18. The method of claim 11, wherein the color characteristic profile is stored in a transmissable data object.

19. The method of claim 18, wherein the transmissable data object is operable to automatically activate the mapping at a second network site in the networked media.

20. The method of claim 11, wherein the networked media comprises the Internet.

21. A computer readable vision characteristic profile for the adjustment of a color scheme in a networked media, comprising:
    a vision characteristic profile, generated by interrogating a user via a user interface at a first location, the vision characteristic profile being readable by a color translation engine at a second location to generate a mapping from a first color scheme in a first site at a third location in a networked media to a second color scheme according to the vision characteristic profile, where the first location, the second location and the third location are remote from one other.

22. A system for processing a vision characteristic profile to adjust a color scheme in a networked media, comprising:
    an input module to receive a vision characteristic profile for a user at a first location; and
    an interface to a color translation engine at a second location, communicating with the input module, the color translation engine generating a mapping from a first color scheme in a first site at a third location in a networked media to a second color scheme according to the vision characteristic profile, where the first location, the second location and the third location are remote from one other.

23. The system of claim 22, wherein the input module comprises at least one of a plug-in for a Web browser and a linkable element on the first site.

24. A method for processing a vision characteristic profile to adjust a color scheme in a networked media, comprising:
    a) receiving a vision characteristic profile for a user at a first location; and
    b) generating at a second location a mapping from a first color scheme in a first site at a third location in a networked media to a second color scheme according to the vision characteristic profile, where the first location, the second location and the third location are remote from one another.

25. The method of claim 24, wherein the step (a) of receiving comprises a step c) of accessing at least one of a plug-in for a Web browser and a linkable element on the first site.

26. A system for generating a vision characteristic profile to adjust a color scheme in a networked media, comprising:
    an interrogation module at a first location to interrogate a user for color response information via a user interface; and
    a generator module at a second location, communicating with the interrogation module, the generator module processing the color response information to generate a color characteristic profile for use at a third location for the user, where the first location, the second location and the third location are remote from one another.

27. The system of claim 26, wherein the user interface comprises a Web-enabled query sequence.

28. The system of claim 26, wherein the interrogation module comprises a sequence of color test templates.

29. A method of generating a vision characteristic profile to adjust a color scheme in a networked media, comprising:

a) interrogating a user at a first location for color response information via a user interface; and b) processing the color response information at a second location to generate a color characteristic profile for use at a third location for the user, where the first location, the second location and the third location are remote from one another.

30. The method of claim 29, wherein the step (a) of interrogating comprises a step (c) of presenting a Web-enabled query sequence.

31. The method of claim 29, wherein the step (a) of interrogating comprises a step (d) of presenting a sequence of color test templates.

* * * * *